(12) United States Patent
Huet (10) Patent No.: US 9,017,300 B2
(45) Date of Patent: Apr. 28, 2015

(54) KIT FOR INJECTING LIQUID INTO A PATIENT AND ASSOCIATED PREPARATION METHOD

(75) Inventor: Gildas Huet, Ivry le Temple (FR)

(73) Assignee: Perouse Medical, Ivry le Temple (FR)

( * ) Notice: Subject to any disclaimer, the term of this patent is extended or adjusted under 35 U.S.C. 154(b) by 248 days.

(21) Appl. No.: 13/100,423

(22) Filed: May 4, 2011

(65) Prior Publication Data

US 2011/0301570 A1 Dec. 8, 2011

(30) Foreign Application Priority Data

May 5, 2010 (FR) ...................................... 1053498

(51) Int. Cl.
*A61M 37/00* (2006.01)
*A61M 5/142* (2006.01)
*A61M 39/02* (2006.01)
*A61M 5/158* (2006.01)

(52) U.S. Cl.
CPC ........... *A61M 5/14276* (2013.01); *A61M 5/158* (2013.01); *A61M 39/0208* (2013.01)

(58) Field of Classification Search
USPC ...................... 604/288.01–288.04, 131, 890.1
See application file for complete search history.

(56) References Cited

U.S. PATENT DOCUMENTS

| 6,360,784 B1 | 3/2002 | Philippens et al. |
| 7,169,292 B2 * | 1/2007 | Chae et al. .................... 208/130 |
| 2006/0259012 A1 | 11/2006 | Propp et al. |
| 2009/0227951 A1 * | 9/2009 | Powers et al. ................. 604/116 |

FOREIGN PATENT DOCUMENTS

| EP | 1527794 A1 | 5/2005 |
| FR | 2658082 | 8/1991 |
| FR | 2802821 A1 | 6/2001 |
| FR | 2869806 | 11/2005 |
| FR | 2886857 | 12/2006 |
| JP | 2005-131414 A | 5/2005 |
| JP | 2008-539025 A | 11/2008 |
| WO | 2006/116438 A2 | 11/2006 |

OTHER PUBLICATIONS

FR1001869: Rapport de Recherche Preliminaire Partiel, Institut National de la Properiete Industrielle, 4 pages, Dec. 20, 2010.

* cited by examiner

*Primary Examiner* — Kevin C Sirmons
*Assistant Examiner* — Deanna K Hall
(74) *Attorney, Agent, or Firm* — McDermott Will & Emery LLP (57) ABSTRACT

This kit includes an injection device comprising a needle having a free end pricked into a septum of an implantable chamber and an intermediate tubing connected downstream to the needle. The kit includes an upstream conduit having an upstream end connected to a liquid dispensing apparatus and a downstream end removably connected to the intermediate tubing. The pressure loss through the upstream conduit is greater than 25% of the total pressure loss taken between the upstream end of the upstream conduit and the free end of the needle, upon injecting liquid through the upstream conduit and the injection device.

12 Claims, 5 Drawing Sheets

KIT FOR INJECTING LIQUID INTO A PATIENT AND ASSOCIATED PREPARATION METHOD

CROSS-REFERENCE TO RELATED APPLICATIONS

This application claims priority to French Application No. 10 53498 filed on May 5, 2010. The above-identified patent application is incorporated herein, by reference, in its entirety.

FIELD OF THE INVENTION

The present invention relates to a kit for injecting liquid into a patient, of the type comprising:
- an implantable chamber comprising a hollow base body, a septum obturating the base body and a conduit for discharging fluid out of the base body;
- an injection device with a needle comprising a needle having a free end intended to be pricked into the septum and an intermediate tubing connected downstream to the needle;
- an upstream conduit having an upstream end intended to be connected to a liquid dispensing apparatus and a downstream end removably connected to the intermediate tubing.

BACKGROUND OF THE INVENTION

Such a kit is notably intended for injecting fluid into a patient, for example in the field of oncology or during the injection of a contrast product into a patient, in order to achieve the taking of a medical image.

This image may be used for non-invasive evaluation of the characteristics of the vascular system of the patient, for example for performing an angiography by computer tomography, designated as "CT".

In the latter case, it is necessary to inject very rapidly with a high flow rate, a contrast product into the vascular system of the patient, with which a sufficiently high concentration may be obtained in order to have sufficient contrast during the full scanning time which is of the order of 30 to 45 seconds.

In order to facilitate the injection of a contrast product at a high flow rate into the vascular system of the patient, the use of a kit of the aforementioned type is known, including a chamber implanted under the skin of the patient. The chamber defines an injection point in the patient, which is located away from the blood circulation conduit into which the product has to be injected. This avoids deteriorating the blood circulation conduit by repeated pricks through this conduit.

In a known way, such a chamber includes a hollow body obturated by a flexible septum and a conduit for evacuating liquid out of the hollow body. The discharge conduit protrudes from the hollow body as far as the injection point into the vascular system.

In order to inject the liquid into the patient, the practitioner connects the outlet of the liquid dispensing apparatus to the needle injection device. And he/she then introduces the needle of the device into the chamber through the septum. He/she then triggers injection of liquid from the injection apparatus through the injection device and the chamber.

In order to guarantee introduction of liquid at a very high flow rate, for example greater than 1 ml/s, it is necessary to substantially increase the pressure at the outlet of the injection apparatus. This outlet pressure may for example be greater than 18 bars.

Nevertheless, because of their design, the implantable chambers have a maximum pressure of use which is generally much lower than the pressure of the liquid delivered by the injection apparatus, for example equal to about 8 bars. In applications where the fluid is injected at a very high flow rate, there therefore exists a substantial risk that the chamber does not withstand the internal pressure of the fluid from the dispensing apparatus.

In order to limit the risk incurred by the patient, the American patent application US 2009/0227951 describes a kit in which the needle injection device has a substantial pressure loss of the order of about fifteen bars. Such an injection device therefore guarantees the safety of the patient, while providing a high pressure loss.

Such an injection device should however be designed specifically for high flow rate injections and cannot be used for other injections of products, notably at lower flow rates in which the pressure at the outlet of the injection apparatus is lower. This therefore increases the cost of the aforementioned kit and limits its possibilities of use.

SUMMARY OF THE INVENTION

An object of the invention is therefore to obtain a low cost kit for injecting liquid into a patient, but which nevertheless allows high flow rate injection of liquid to be carried out in a patient, while guaranteeing the safety of the patient.

For this purpose, the object of the invention is a kit of the aforementioned type, characterized in that the pressure loss through the upstream conduit, taken between its upstream end and its downstream end is greater than 25% of the total pressure loss taken between the upstream end of the upstream conduit and the free end of the needle, during the injection of liquid through the upstream conduit and the injection device, advantageously between 25 and 45% of the total pressure loss.

The kit according to the invention may comprise one or more of the following features, taken individually or according to any technical possible combination(s):
- the pressure loss between the upstream end of the upstream conduit and the downstream end of the upstream conduit is greater than 30% of the total pressure loss between the upstream end of the upstream conduit and the free end of the needle and is notably comprised between 30% and 45% of the total pressure loss;
- the pressure loss through the needle injection device is less than four times the pressure loss through the chamber when the needle is pricked into the chamber;
- the pressure loss between the upstream end of the upstream conduit and the free end of the needle is greater than four times the pressure loss through the chamber;
- the length of the upstream conduit is greater than six times the length of the intermediate tubing;
- the average inner diameter for letting through fluid within the upstream conduit is less than or equal to 150% of the average inner diameter for letting through fluid within the intermediate tubing;
- the upstream conduit includes an upstream tubing delimiting a passage for circulation of fluid and protrusions increasing the pressure loss, positioned in the passage for circulation of fluid; and
- the upstream conduit comprises an upstream tubing and at least one pressure loss unit interposed on the upstream tubing.

The object of the invention is also a method for preparing a kit for injecting liquid into a patient, with view to injecting liquid into an implantable chamber positioned in the patient, the implantable chamber comprising a hollow base body, a septum obturating the base body and a conduit for discharging liquid out of the base body, the method having the following steps: providing an injection device with a needle, the device comprising a needle having a free end intended to be pricked into the septum and an intermediate tubing connected downstream to the needle; providing an upstream conduit comprising an upstream end intended to be connected to a liquid dispensing apparatus and a downstream end intended to be removably connected to the intermediate tubing, so that the pressure loss between the upstream end of the upstream conduit and the downstream end of the upstream conduit is greater than 25% of the total pressure loss between the upstream end of the upstream conduit and the free end of the needle; and connecting the downstream end of the upstream conduit to the intermediate tubing.

The method according to the invention may comprise one or more of the following features, taken individually or according to any technically possible combinations: the method further comprises a step for adjusting the injection flow rate of the liquid dispensing apparatus, notably before injecting liquid into the patient, to a value greater or equal to 1 mL/s; and the pressure loss between the upstream end of the upstream conduit and the free end of the needle is greater than ten bars.

The object of the invention is also a method for injecting a liquid, advantageously a non-therapeutic liquid, notably a diagnostic product such as a contrast product for medical imaging, into a patient, the method being of the type having the following steps: providing an upstream conduit having an upstream end and a downstream end; connecting the upstream end of the upstream conduit to a liquid dispensing apparatus and the downstream end of the upstream conduit to a needle injection device comprising a needle having a free end, the free end of the needle being intended to be pricked into a septum of an implantable chamber comprising a hollow base body, the septum obturating the hollow base body; and injecting liquid from the dispensing apparatus through the upstream conduit, the needle injection device, and the implantable chamber, the pressure loss between the upstream end of the upstream conduit and the downstream end of the upstream conduit being greater than 25% of the pressure loss between the upstream end of the upstream conduit and the free end of the needle.

BRIEF DESCRIPTION OF THE DRAWINGS

The invention will be better understood upon reading the description which follows, only given as an example, and made with reference to the appended drawings, wherein.

DETAILED DESCRIPTION OF THE INVENTION

In all the following, the terms of "upstream" and "downstream" are generally meant with respect to the normal direction of circulation of a fluid during its injection.

Figure 3:
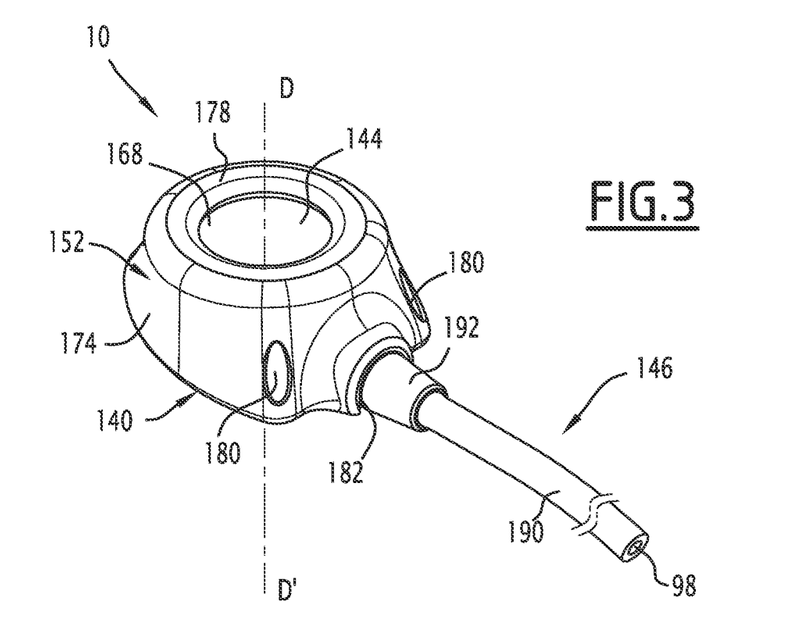
FIG. 3 is a perspective view of the implantable chamber of the kit of FIG. 1.

A first kit 10 for injecting liquid into a patient 11 is illustrated in FIG. 3. Such a kit 10 is notably intended to inject a liquid at a high flow rate into the vascular system of the patient, for example at a flow rate of greater than 1 mL/second, advantageously equal to 5 mL/second.

The injected liquid is for example a drug. Alternatively, the injected liquid is a non-therapeutic liquid such as a diagnostic product notably a contrast product for medical imaging. With the contrast product, an image of the vascular system of the patient may be produced, for example by computer tomography.

The injected liquid has a viscosity advantageously comprised between 1 mPa·s and 20 mPa·s.

Figure 1:
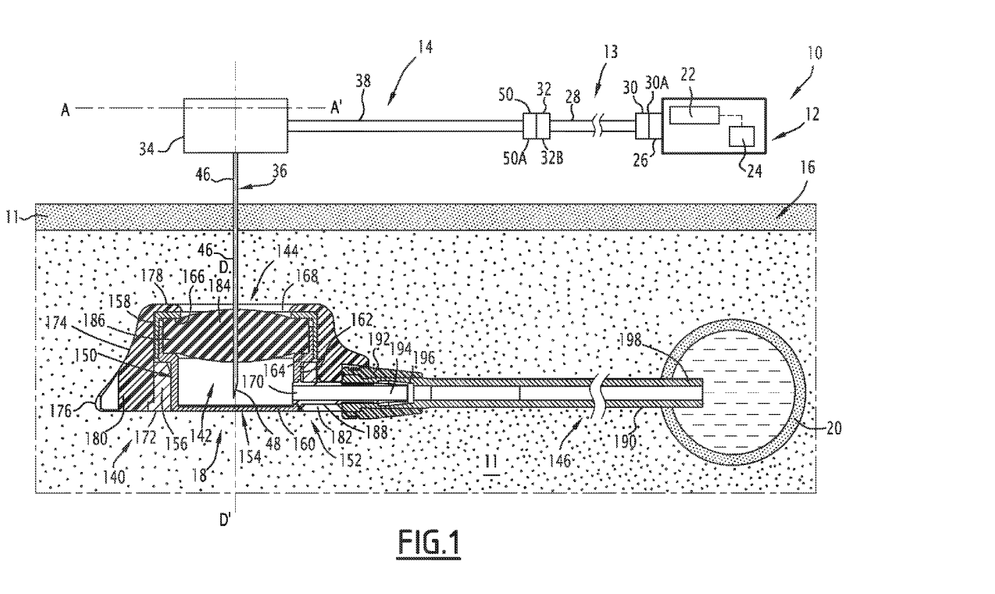
FIG. 1 is a schematic sectional view of a first injection kit according to the invention during its use.

The kit 10 comprises from upstream to downstream, a liquid dispensing apparatus 12, placed outside the body of the patient 11, an upstream conduit 13, an injection device 14 with a needle intended to be inserted through the skin 16 of the patient 11, and an implantable chamber 18 according to the invention, positioned under the skin 16 of the patient and hydraulically connected downstream to a blood circulation conduit 20.

The dispensing apparatus 12 comprises a pump 22 for example with a cylinder, capable of dispensing a liquid with an adjustable flow rate. The injection apparatus 12 advantageously comprises a unit 24 for adjusting the volume flow rate of the pump, capable of being actuated by a user.

The cylinder pump 22 of the dispensing apparatus 12 comprises an outlet endpiece 26 intended to removably receive the upstream conduit 13.

The upstream conduit 13 comprises an upstream flexible tubing 28, an upstream fitting 30 positioned at an upstream end 30A of the tubing 28 and a downstream fitting 32 positioned at the downstream end 32A of the tubing 28.

The length of the upstream conduit is greater to 1.5 m and is for example comprised between 1.5 m and 2.5 m.

The inner diameter for letting through the fluid is advantageously less than 1.5 mm, as this will be seen below.

Figure 2:
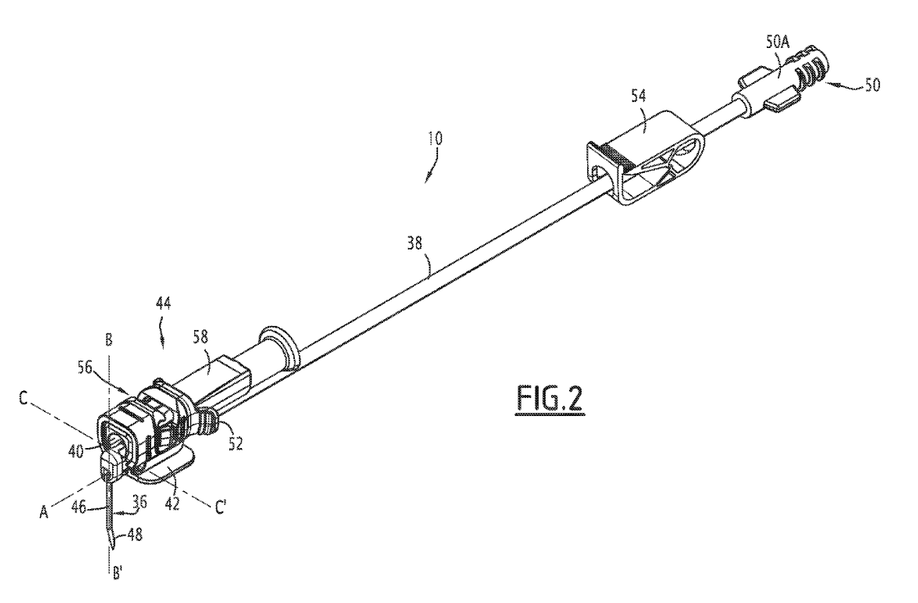
FIG. 2 is a perspective view of an exemplary injection device with a needle which may be used in the kit of FIG. 1.

The needle device 14 is for example of the type described in French applications FR 2 869 806 or FR 2 886 857 of the Applicant. It comprises a needle support 34, a needle 36 borne by the support and an intermediate tubing 38 intended to connect the needle 36 to the upstream conduit.

The support 34 comprises a core 40 receiving the needle 36 and the downstream end of the intermediate tubing 38, supporting fins 42 intended to be applied on the skin of the patient, and in the example illustrated in FIG. 2, an optional needle protection assembly 44 permanently mounted on the core 40.

The core 40 is made on the basis of a rigid body extending along a longitudinal axis A-A'.

The supporting fins 42 protrude transversely relatively to the axis A-A' on either side of the core 40.

The core 40 delimits an internal passage for receiving an upstream segment of the needle 36 and the downstream end of the tubing 38.

The needle 36 is advantageously a bent needle, a so-called "Huber" needle. This needle 36 comprises an upstream segment 35 positioned in the core 40, and a downstream segment 46 protruding along an axis B-B' perpendicular to the axis A-A' of the core 40 so as to be pricked into the skin 11 of the patient.

The downstream segment 46 of the needle 36 has a bevelled free end 48 for facilitating penetration of the needle 36 through the skin 11 and its introduction into the chamber 18.

The intermediate tubing 38 is permanently fixed in the needle support 34. It extends between an upstream end 50A provided with a fitting 50 and a downstream end 52 permanently connected to the upstream segment 35 of the needle 36 in the core 40.

The tubing 38 is advantageously provided with an obturation unit formed by a clamp 54 capable of cutting off the flow of circulating fluid through the tubing 38 or of reducing it.

The protective assembly 44 illustrated in FIG. 2 is optional. This assembly 44 is described in detail in French application FR 2 886 857. It comprises a base 56 jointed around the core 40 and a hollow pusher 58 slidably mounted in the base 52 order to swallow the downstream segment 46 of the needle 36 during its withdrawal.

As described in detail in FR 2 886 857, the base 56 and the pusher 58 are mobile around the axis C-C' between a laid-down configuration for injecting product into the patient illustrated in FIG. 2 and an erected configuration for extracting the needle in the hollow pusher 58.

According to the invention, the upstream conduit 13 and the injection device 14 are dimensioned so that the pressure loss ΔPa through the upstream conduit 13, taken between the upstream end 30A and the downstream end 32B of the upper stream 13 is greater than 25% of the total pressure loss ΔPb through the upstream conduit 13 and the injection device 14, taken between the upstream end 30A of the upstream conduit 13 and the free end 48 of the needle.

Thus, for example, when the pressure delivered by the pump of the apparatus 12 is greater than 16 bars, for a fluid flow rate delivered by the upper pump of 5 mL/s, the pressure loss ΔPa through the upstream conduit 13 is greater than 4 bars, for a total pressure loss ΔPb through the upstream conduit 13 and the device 14 of greater than 12 bars.

Advantageously, the pressure loss ΔPa through the conduit 13 is comprised between 25% and 60% of the total pressure loss ΔPb through the conduit 13 and the device 14, and notably between 25% and 45%, advantageously between 30% and 45% of this total pressure loss.

Figure 4:
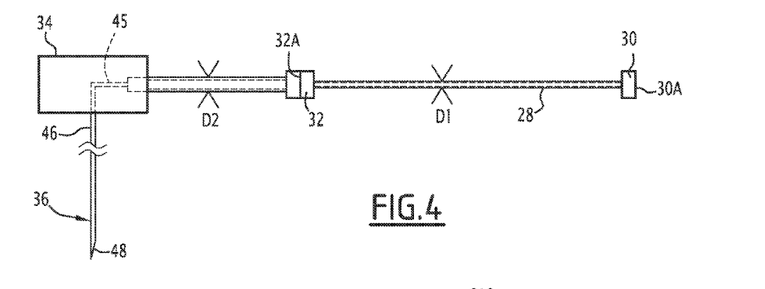
FIG. 4 is a schematic view illustrating the first kit according to the invention.

For this purpose, in a first embodiment schematically illustrated in FIG. 4, the inner diameter D1 for letting through fluid through the upstream tubing 28 is less than or equal to 150%, notably less than 100%, of the inner diameter D2 of the passage through the tubing 38.

For example, when the diameter D2 of the tubing 38 is comprised between 1 mm and 1.5 mm, the inner diameter D1 of the tubing 28 is comprised between 1.5 mm and 1.3 mm.

As this will be seen below, this pressure loss within the upstream conduit 13 guarantees that the fluid pressure in the chamber 18 is less than a given safety value when the needle 36 is pricked into the chamber 18, in spite of the large inner section of the intermediate tubing 38 and in spite of the relatively low pressure loss through the needle 36.

Moreover, the pressure loss through the needle injection device 14 is less than three times, notably less than four times the pressure loss through the chamber 18 when the needle 36 is pricked into the chamber.

Further, the pressure loss between the upstream end 30A of the upstream conduit 13 and the free end 48 of the needle 36 is greater than four times the pressure loss through the chamber 18.

In order to measure these pressure losses, the following method may be applied: either by simulating fluid flow or by simulating injection in vitro while placing pressure sensors at suitable locations. The fluid used for measuring the pressure loss has a viscosity equal to 10 mPa·s.

As illustrated by FIGS. 1 to 3, the chamber 18 includes a base body 140 delimiting an inner volume 142 for receiving liquid, a septum 144 obturating the inner volume 142 and intended to be pricked by the needle 36, and a conduit 146 for discharging the liquid out of the inner volume 142 towards the blood circulation conduit 20.

The base body 140 includes an inner container 150 with a central axis D-D' and an outer peripheral shell 152 which, in this example, is snap-fastened onto the inner container 150.

In this example, the container 150 comprises a metal tank 154 for receiving liquid, a lower insert 156 mounted around the tank 154 and a retaining ring 158 of the septum 144 positioned above the tank 154. Alternatively, the tank 154, the insert 156 and the ring 158 are made in a single piece.

The tank 154 is for example formed in titanium. It includes a bottom 160 which delimits the bottom of the inner volume 142 and partly that of the chamber 18 and a substantially cylindrical sidewall 162 which laterally delimits the inner volume 142.

The sidewall 162 has an annular shoulder 164 supporting the septum 144 which extends along its upper edge.

The insert 156 extends around the sidewall 162 of the tank 154, under the annular shoulder 164.

The ring 158 extends facing the annular shoulder 164 and defines an upper surface 166 for tightening the septum 144.

The inner volume 142 is delimited between the sidewall 162 and the bottom of the tank 154. The volume 142 opens upwards through a main upper aperture 168 receiving the septum 144, it opens laterally through the sidewall 162 of the tank through a radial aperture 170 for discharging product. The radial aperture 170 has a smaller section than the section of the main aperture 168.

The insert 156 delimits a radial passage through which extends the conduit 146.

The peripheral shell 152 is made in plastic material, for example in polyoxymethylene or POM. It extends around the insert 156 and the ring 158, in order to hold the ring 158 and the insert 156 in position on the tank 154.

The shell 152 has a lower surface 172 which is flush with the bottom 160 of the container 150 and a concave upper surface 174 which converges, from top to bottom, from the ring 158 towards a peripheral edge 176 of the shell 152 located at the lower surface 172.

The shell 152 has a peripheral lip 178 substantially parallel to the lower surface 172 which bears upon the ring 158 around the main aperture 168.

The peripheral edge 176 delimits the outer contour of the chamber 18. In this example, this contour is of a substantially triangular shape.

The peripheral shell 152 further delimits through-apertures 180 for letting through a suture thread and a radial aperture 182 for letting through the liquid discharging conduit 146.

Passage apertures 180 connect the upper surface 174 to the lower surface 172 in the vicinity of the peripheral edge 176, substantially parallel to the axis D-D'. They are angularly distributed around the axis D-D'. The radial aperture 182 opens out facing the discharge aperture 170 which it radially extends relatively to the D-D' axis.

The septum 144 is for example made on the basis of a flexible plastic material such as silicone. It has a central portion 184 obturating the main aperture 168 and a peripheral portion 186 hemmed in between the annular shoulder 164 and the lower surface 166 of the ring 158. The main portion 184 has a greater height than that of the peripheral portion.

The septum 144 sealably obturates the inner volume 142 outwards.

The discharge conduit 146 comprises a rigid fitting 188, a flexible tubing 192 and a crimping ring 192 of the flexible tubing 190 on the rigid fitting 188.

It radially protrudes with respect to the base body 140 through the radial aperture 182 and beyond this radial aperture 182.

The rigid fitting 188 is formed by a hollow rod 194 assembled on the outer wall 162 of the container around the discharge aperture 170. The hollow rod 194 radially protrudes through the radial aperture 182 outside the base body 140.

The tubing 190 is made on the basis of a flexible plastic material. It has a greater length than the maximum transverse extent of the base body 140, for example at least twice greater than this maximum extent.

The tubing 190 extends between an upstream end 196 force-fitted around the free end of the rigid fitting 188 and a downstream free end 198 intended to be placed in the blood circulation conduit 20.

The crimping ring 192 is force-mounted in the radial aperture 182 for crimping the flexible tubing 190 against the hollow rod 194. It protrudes radially beyond the base body 140 over a smaller length than that of the tubing 190, for example at least twice smaller than that of the tubing 190.

The operation of the first kit 10 according to the invention will now be described.

Initially, the implantable chamber 18 was surgically positioned under the skin of the patient 16. For this purpose, the chamber 18 is applied against tissues of the patient and is held in position by suturing it through the passage apertures 180. The septum 144 is then placed facing the skin 16, in the vicinity of the latter in order to easily receive the injection needle 36 of the device 14.

The flexible tubing 190 is deployed in the body of the patient in order to place its free end 198 in the vascular system of the patient, for example in a blood circulation conduit 20.

And the skin 16 of the patient is then put back into place, so that the chamber 18 is partly or totally masked by the skin 16.

When a fluid injection has to be performed in the patient, the practitioner first of all performs radiography of the patient in order to view the exact position of the chamber 18 and to determine its characteristics, notably the injection flow rate or the maximum pressure.

And then he/she adjusts the unit for adjusting the flow rate 24 to a flow rate of less than or equal to the maximum flow rate allowed by the chamber 18.

Next, the practitioner selects an upstream conduit 13 and an injection device 14 as defined above.

The practitioner connects the upstream fitting 30 located at the upstream end 30A of the upstream conduit 13 to the outlet end piece 26 of the injection apparatus 12.

He/she then connects the intermediate tubing 38 to the upstream conduit 13 by mounting the fitting 50 located at the upstream end 50A of the intermediate tubing 38 onto the downstream fitting 32 located at the downstream end 38B of the upstream tubing 28.

The presence of the upstream conduit 13 selected so that the pressure loss $\Delta Pa$ through this conduit 13 is greater than at least 25% of the total pressure loss $\Delta Pb$ through the conduit 13 and the injection device 14, guarantees that the total pressure loss $\Delta Pb$ will be sufficiently large for ensuring the safety of the patient, notably by avoiding that the pressure of the chamber exceeds the maximum pressure Ps which this high flow rate injection chamber withstands.

This guarantee is ensured even if the injection device 14 is not specifically intended for high flow rate injections. This allows use of a standardized injection device at a lower cost.

Next, the practitioner sticks the needle 36 through the skin 16 of the patient 11 and through the septum 144, by grasping the needle support 34 in order to bring the free end 48 of the needle 36 into the inner volume 142.

A continuous fluidic path is then established from the injection apparatus 12 through the outlet piece 26, the upstream tubing 28, the intermediate tubing 38, the needle 36, the inner volume 142, the discharge aperture 170, and the downstream channel defined in the discharge conduit 146 as far as a free end 198 of tubing 190.

Figure 8:
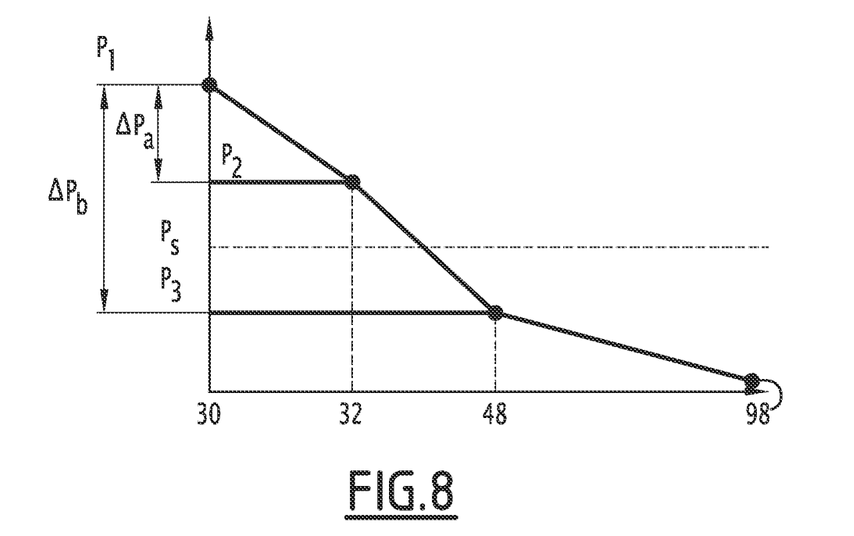
FIG. 8 is a graph schematically illustrating the pressure loss through a kit according to the invention during injection of fluid through this kit.

The practitioner may then safely inject liquid into the patient notably at a high flow rate of more than 1 mL/s, notably more than 4 mL/s As illustrated by FIG. 8, although the injection pressure P1, taken at the outlet of the injection apparatus 12 is greater than four times the maximum pressure Ps tolerated by the chamber 18, the upstream conduit 13 is designed so as to significantly reduce the pressure P2 taken at its outlet.

This guarantees that the pressure P3, taken in the chamber 42 at the free end of the needle 48 is much less than the safety pressure Ps, even if the injection device 14 has low pressure loss.

The injection device 14 may therefore be used not only for high pressure applications, with an upstream conduit 13 which guarantees the safety of the patient, but also for applications with much lower injection pressures, without any upstream conduit 13, or with an upstream conduit with low pressure loss.

The cost of the injection device 14, and therefore of the kit 10, may be accordingly reduced, since a standard injection device may be manufactured both for high pressure and low pressure applications.

In the case of an injection at a pressure of about 0.1 bar relatively to the outlet of the injection apparatus 12, the flow rate through the chamber 18 may be greater than 0.5 mL/s. In spite of the low entry pressure, this flow rate is for example greater than 0.6 mL/s In the second injection kit 210 illustrated in FIG. 5, the internal diameter D1 of the upstream tubing 28 is not necessarily less than 150% of the internal diameter D2 of the intermediate tubing 38.

Figure 5:
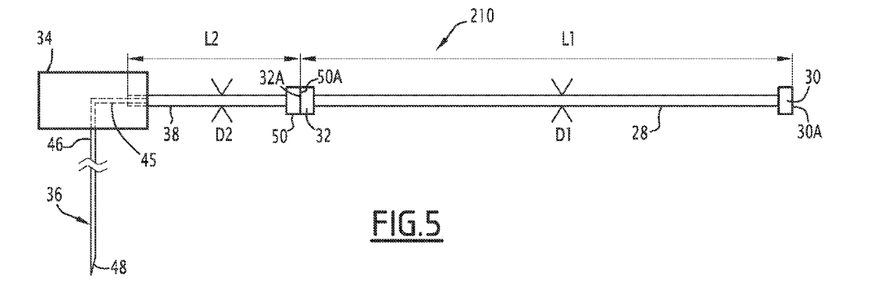
FIG. 5 is view analogous to FIG. 4 for a second kit according to the invention.

In this respect, the length L1 of the upstream tubing 28 is increased and is selected so as to be greater for example than at least six times the length L2 of the intermediate tubing 38.

Figures 6, 7:
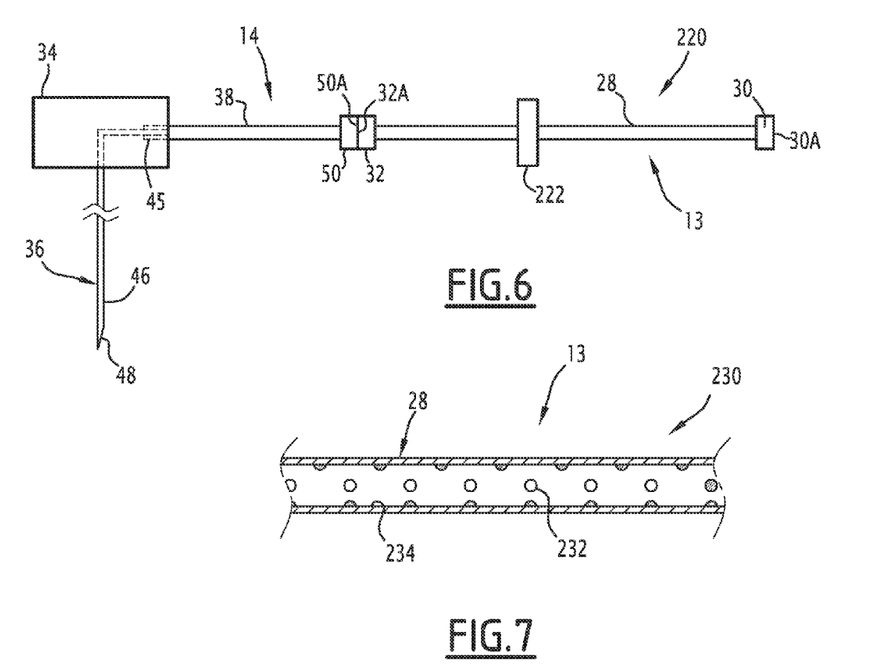
FIG. 6 is a view analogous to FIG. 4 for a third kit according to the invention.
FIG. 7 is a partial sectional view illustrating the upstream conduit of a fourth kit according to the invention.

In the third injection kit 220 according to the invention, the upstream conduit 13 is provided with an intermediate element 222, for example formed by a filter, which allows an increase in its pressure loss so that the pressure loss through the upstream conduit 13 is greater than 25% of the pressure loss through the upstream conduit 13 and the injection device 14.

For this purpose, the pressure loss through the filter 222 is for example greater than 2.5 bars.

The operation of the third kit 220 according to the invention is analogous to that of the first kit 10.

The upstream tubing 28 of a fourth injection kit 230 according to the invention is illustrated in FIG. 7. Unlike the upstream tubing 28 of the first kit 10, this tubing is provided with elements 232 which protrude in the interior passage delimited by the upstream tubing 28 so that the pressure loss through the upstream conduit 13 is greater than 25% of the pressure loss through the upstream conduit 13 and the injection device 14.

In the example illustrated in FIG. 7, the protruding elements 232 are formed by spikes which protrude radially towards the axis of the tubing 28.

The operation of the third kit 230 according to the invention is moreover analogous to that of the first kit 10.

As described above, the pressure losses may be measured unambiguously by simulation of fluid flow or by simulation of injection in vitro by placing pressure sensors at the suitable locations. In the first case, software packages of the FLUENT, COMSOL, CODE SATURNE type may be used. Moreover, in the case of simulations of injection in vitro, the fluid flow rate may be set to 5 ml/s and the viscosity to 10 mPa·s.

Another way for determining the pressure losses may be the use of Poiseuille's law which defines the pressure loss generated by laminar flow in a conduit versus the diameter, the length, the fluid flow rate and the viscosity.

As indicated above, the fluid flow rate is set to 5 mL/s and the viscosity is selected to be 10 mPa·s.

Particular exemplary embodiments of the invention will now be described.

EXAMPLE 1

An injection device 14 with a needle of the Polyperf Safe® 603011 type, marketed by PEROUSE MEDICAL is used. This device 14 comprises a needle 36 and an intermediate tubing 38. The measured pressure loss through this needle injection device, between the free end 48 of the needle and the upstream end of the intermediate tubing 38 is 3.32 bars.

In order to obtain an upstream conduit 13 having a pressure loss, taken between its upstream end 30A and its downstream end 32B, of more than 25% of the total pressure loss, taken between the upstream end 30A of the upstream conduit 13 and the free end of the needle 36, the upstream conduit 13 has an internal diameter of 2.2 mm and a length of 127 cm long. In this case, the pressure loss generated through the upstream conduit 13 is 1.1 bar. It represents about 25% of the total pressure loss.

EXAMPLE 2

In this example, a device 14 of the Polyperf Safe® 601509 type, marketed by PEROUSE MEDICAL is used. This needle injection device 14 has a pressure loss of 3.95 bars. In this case, the upstream conduit 13 has a diameter of 2.2 mm and a length of 151 cm. For such a length, the upstream conduit 13 generates a pressure loss of 1.31 bar which is substantially equal to 25% of the total pressure loss.

EXAMPLE 3

The needle injection device 14 is of the Polyperf Safe® 601507 type, marketed by PEROUSE MEDICAL. This needle device 14 has a pressure loss of 3.90 bars. The upstream conduit 13 is then selected with an internal diameter of 1.5 mm and a length of 134 cm, which generates a pressure loss of 1.30 bar.

EXAMPLE 4

The same device 14 as in Example 1 is used. The upstream conduit 13 has an internal diameter of 1.2 mm and a length of 139 cm. The pressure loss through the upstream conduit 13, taken between its upstream end and its downstream end is substantially equal to 13.7 bars i.e. 80% of the total pressure loss taken between the upstream end 30A of the upstream conduit 13 and the free end 48 of the needle 36.

EXAMPLE 5

The same device 14 as in Example 2 is used. An upstream conduit 13 having an internal diameter of 1.2 mm and a length of 133 cm is used. The pressure loss through the upstream conduit 13 is substantially equal to 13.0 bars, which represents 76% of the total pressure loss, taken between the upstream end 30A of the upstream conduit 13 and the free end 48 of the needle 36.

EXAMPLE 6

The same device 14 as in Example 3 is used. The upstream conduit 13 has a diameter of 0.8 mm and a length of 110 cm long, which generates a pressure loss of 13.1 bars. This pressure loss represents about 77% of the total pressure loss, taken between the upstream end 30A of the upstream conduit 13 and the free end 48 of the needle 36.

These preceding examples illustrate the fact that the parameters required for obtaining a kit according to the invention, wherein the pressure loss through the upstream conduit, taken between its upstream end and its downstream end is greater than 25% of the total pressure loss, taken between the upstream end of the upstream conduit and the free end of the needle, may be determined according to the relevant injection device 14.

The invention claimed is:

1. A kit for injecting liquid in a patient, comprising:
    an injection device with a needle, comprising a needle having a free end intended to be pricked into a septum of an implantable chamber comprising a hollow base body, the septum obturating the base body, and the chamber including a conduit for discharging fluid out of the base body; the injection device including an intermediate tubing connected downstream to the needle;
    an upstream conduit having an upstream end intended to be connected to a liquid dispensing apparatus and a downstream end removably connected to the intermediate tubing,
    characterized in that the pressure loss through the upstream conduit, taken between the upstream end and the downstream end, is greater than 25% of the total pressure loss taken between the upstream end of the upstream conduit and the free end of the needle, during injection of liquid through the upstream conduit and the injection device.

2. The kit according to claim 1, wherein the pressure loss between the upstream end of the upstream conduit and the downstream end of the upstream conduit is greater than 30% of the total pressure loss between the upstream end of the upstream conduit and the free end of the needle and is notably comprised between 30% and 45% of the total pressure loss.

3. The kit according to claim 1, further comprising an implantable chamber comprising a hollow base body, the septum obturating the base body, and the chamber including a conduit for discharging fluid out of the base body.

4. The kit according to claim 1, wherein the pressure loss through the needle injection device is less than four times the pressure loss through the chamber when the needle is pricked into the chamber.

5. The kit according to claim 3, characterized in that the pressure loss between the upstream end of the upstream conduit and the free end of the needle is greater than four times the pressure loss through the chamber.

6. The kit according to claim 1, characterized in that the length of the upstream conduit is greater than six times the length of the intermediate tubing.

7. The kit according to claim 1, wherein an average inner diameter for letting through fluid within the upstream conduit is less than or equal to 150% of the average inner diameter for letting through fluid within the intermediate tubing.

8. The kit according to claim 1, characterized in that the upstream conduit includes an upstream tubing delimiting a passage for circulation of fluid and protrusions for increasing the pressure loss, and positioned in the fluid circulation passage.

9. The kit according to claim 1, wherein the upstream conduit comprises an upstream tubing and at least one pressure loss unit interposed on the upstream tubing.

10. A method for preparing a kit for injecting liquid into a patient, with view to injecting liquid into an implantable chamber positioned in the patient, the implantable chamber comprising a hollow base body, a septum obturating the base body and a conduit for discharging liquid out of the base body, the method being of the type comprising the following steps:

providing a needle injection device, the device comprising a needle having a free end intended to be pricked into the septum and an intermediate tubing connected downstream to the needle;

providing an upstream conduit comprising an upstream end intended to be connected to a liquid dispensing apparatus and a downstream end intended to be removably connected to the intermediate tubing, so that the pressure loss between the upstream end of the upstream conduit and the downstream end of the upstream conduit is greater than 25% of the total pressure loss between the upstream end of the upstream conduit and the free end of the needle; and connecting the downstream end of the upstream conduit onto the intermediate tubing.

11. The method according to claim 10, further comprising a step for adjusting the injection flow rate of the liquid dispensing apparatus, notably before injecting liquid into the patient, at a value greater than or equal to 1 mL/s.

12. The method according to claim 10, characterized in that the pressure loss between the upstream end of the upstream conduit and the free end of the needle is greater than ten bars.

* * * * *